(12) United States Patent
Rabinowitz

(10) Patent No.: US 7,226,624 B2
(45) Date of Patent: *Jun. 5, 2007

(54) SYNERGISTIC COMPOSITIONS FROM YEAST-MODIFIED AQUEOUS EXTRACTS FROM ALMOND HULLS

(76) Inventor: Israel N. Rabinowitz, 2534 Foothill Rd., Santa Barbara, CA (US) 93105

( * ) Notice: Subject to any disclaimer, the term of this patent is extended or adjusted under 35 U.S.C. 154(b) by 373 days.

This patent is subject to a terminal disclaimer.

(21) Appl. No.: 10/202,478

(22) Filed: Jul. 24, 2002

(65) Prior Publication Data

US 2004/0018254 A1    Jan. 29, 2004

(51) Int. Cl.
*A61K 36/736* (2006.01)
(52) U.S. Cl. ........................ 424/735; 424/776
(58) Field of Classification Search ........... 424/735, 424/776, 115
See application file for complete search history.

(56) References Cited

U.S. PATENT DOCUMENTS

| 4,457,932 | A | * | 7/1984 | Juby et al. |
| 4,997,489 | A |   | 3/1991 | Rabinowitz |
| 5,064,762 | A |   | 11/1991 | Rabinowitz |
| 5,160,756 | A |   | 11/1992 | Rabinowitz |
| 5,626,847 | A | * | 5/1997 | Agrawal et al. |

OTHER PUBLICATIONS

Calorie Control Council information website regarding sorbitol (http://web.archive.org/web/20010618123828/http://www.caloriecontrol.org/sorbitol.html (Jun. 18, 2001).*

* cited by examiner

*Primary Examiner*—Susan Coe Hoffman
(74) *Attorney, Agent, or Firm*—Donald D. Mon

(57) ABSTRACT

An elixir combining synergistic components, all of which are derived from the same source, namely almond hulls.

2 Claims, No Drawings

SYNERGISTIC COMPOSITIONS FROM YEAST-MODIFIED AQUEOUS EXTRACTS FROM ALMOND HULLS

FIELD OF THE INVENTION

Synergistic compositions obtained from the water extract of almond hulls.

BACKGROUND OF THE INVENTION

The sweet almond is a relative of other stone-containing fruits such as peaches, apricots, and plums. It shares with them the presence of a center stone (the endocarp) and a surrounding flesh layer (the mesocarp). The flesh portion of all of these fruits, including the almond, is edible and enjoyable. However, there is a major difference how they are used in the cultures consuming them.

The peach, apricot and plum are generally eaten fresh, or harvested fresh and dried for later aqueous reconstitution, or eaten as a dried product. The central stone is discarded. Not so with the almond. Generally its end product is the stone, which is the common almond nut that is so widely used, especially in the United States.

In contrast, the almond fruit is only rarely harvested fresh. Instead it is left on the tree to approach senescence and is left to dry on the tree to a low moisture content. Evidently the biological processes undergone by the fruit as it remains on the tree develop quite different phytochemical constituents, the advantages of which have been widely unappreciated.

When the crop is harvested for its nut content, the dried remainder of the mesocarp is removed and becomes what is commonly called the "almond hull". It is regarded as a very low value substance, whose uses are such as for co-generation fuel to be burned in power plants, and a portion of cattle feed ration.

It has been disregarded that the almond hull has a substantial content of sugars, inositol, phytic acid, and many other potentially useful chemicals which are otherwise very difficult and expensive to obtain or produce.

It is an object of this invention to utilize the almond hull as a source of these useful compounds, and to provide processes to produce them inexpensively, using only simple biological and separation procedures to do so.

Interestingly, the relatively large amounts of sugars in the almond hull could be a nuisance in recovering and developing other products. It is an object of this invention instead to utilize the sugars to enhance the production of useful products, at the same time removing them and increasing the harvest of the other products.

Selective separations of the components of the water extract from almond hulls as previously proposed show that as the consequence of suitable yeast processing, a concentrate can be obtained which includes ingredients that synergistically engage sequential processes in the human body. Providing these substances together for previously unsuspected physiological benefits is beyond the contemplation of the skilled person. It is the inventor's opinion that nature itself provides for the desired result, but that in the existing art, the combination is neither known nor available. The applicant has appreciated these advantages, and herein provides processes to produce combinations that were previously not available. The compositions of this invention are readily produced by simple biological procedures from almond hulls.

BRIEF DESCRIPTION OF THE INVENTION

Almond hulls are subjected to water extraction of their soluble constituents. When the fibrous material of the hulls is removed, there remains a water extract which is the subject of this invention. The fibrous residue is of no interest to this instant invention.

The water extract contains inositol, phytic acid, sugars, and of importance to this invention a wide array of other constituents of which some are of individual advantage, and of synergistic advantage when consumed along with others of them.

According to this invention the water extract is subjected to fermentation with a yeast of the type which consumes sugars, thereby leaving after removal of the yeast residues a solution of the remaining constituents, without sugars. The resulting solution is herein referred to as the "treated extract".

The treated extract is concentrated to a syrup, and the syrup is useful as a source of the various constituents thereof, but more importantly as the simultaneous and synergistic nutraceutical components.

This invention will be fully appreciated from the following detailed description, and the accompanying flow diagram.

DETAILED DESCRIPTION OF THE INVENTION

Epidemiological data and experimental results indicate that populations that eat a high proportion of fruits and vegetables in their daily diet, suffer less incidence of cardiovascular disease (CVD), cancers, and diabetes, than populations eating lesser amounts of fruits and vegetables. The biological mechanisms that lead to these results are not completely understood at this time, although anti oxidative activities of the flavonoids, phenolic acids, and polyphenolics found in fruits and vegetables represents the most studied biochemical route for explanation to date.

The hexahydroxy cyclohexane, myo inositol, is also found in at least trace amounts ubiquitously throughout plant and animal kingdoms. Myo inositol is now known to be absolutely essential for normal growth and differentiation and more recently metabolites of myo inositol have been shown to be active at control points of mammalian physiological processes, such that excessively low or high concentrations of these metabolites are implicated in the disease processes of inter alia, bipolar disorder (manic depression disease), diabetes, CVD and certain cancers. The myo inositol metabolites in question are phosphatidyl inositol phosphates, inositol phosphates, and probably also other isomers of myo inositol, as well as other derivatives such as, e.g. pinitol, which is the methyl ether of the isomer chiro inositol.

The mesoderm of the almond fruit (*prunus amygdalus*) as it exists as the almond hull is found to be a particularly rich source of flavonoids, phenolic acids, polyphenolics, myo inositol, inositol phosphates, and other isomers and derivatives of myo inositol, including pinitol and chiro and scyllo inositol.

It is the purpose of this invention to provide combinations of inositol and its metabolites with flavonoids and phenolics, such that their separate and individual beneficial health effects may thereby be synergistically enhanced.

As one example of potential synergy, there is the reported effect of myo inositol and phytic acid (myo inositol hexakisphosphate) in suppression of tumor formation in animal models of human cancer. There is the reported effect of the flavonoids quercitin and genistein in inhibiting growth of human tumor cells, and further, the reported effect of quercitin in inhibiting phosphatidylinositol kinase enzyme, and also lowering cell concentrations of inositol tris phosphate. Quercitin appears to deliver its effect at the interface of the $G_1$ to S phases of the cell cycle. There is, more recently, evidence that the inositol phosphates are involved in nuclear mRNA transport, and therefore, although yet to be definitively shown, are likely also active in $G_1$–S phases of the cell cycle. Quercitin and the inositol phosphates are therefore shown to be potentially effective, taken separately in treatment of certain cancers, and further, there appears to be interaction or "cross talk" between these compounds, such that quercitin is seen to regulate aspects of inositol phosphates metabolism.

A second example of potential synergy, exists in current research and trials of therapeutic molecules in treatment of the disease, cystic fibrosis. A central feature of the disease is impairment of chloride transport in epithelial cells of lungs and intestinal system, including the pancreas. Flavonoids, such as genistein, quercitin, kaempferol, and apigenin, have been shown to stimulate chloride transport and certain of the flavonoids are under investigation, or in initial clinical trials, as potential therapeutic treatments for cystic fibrosis. Also undergoing clinical trials for treatment for cystic fibrosis are certain purinergic agents that initiate several physiologic consequences, including increased inositol phosphates synthesis. Importantly, however, one of the inositol phosphates, inositol (3, 4, 5, 6)P4 has been shown to inhibit chloride conductance in epithelial cells. In light of this latter finding, it has been suggested that an approach to increasing chloride conductance might be to use inositol phosphate analogues which would antagonize the action of inositol. Alternatively, considering the separately useful effects of some of the inositol metabolites, and flavonoids, used separately in treatment of cystic fibrosis, and the regulatory effect of the flavonoids on inositol metabolism, a combination of inositol phosphates and flavonoids, delivered in a temporally regulated manner, might even probably have synergistically enhanced usefulness.

Still another illustration of the interaction between compounds which exhibit anticarcinogenic activity is the currently evolving understanding of the androgen refractory state in prostate cancer therapy. Removal of androgen activity is standard therapy for prostate cancer, but a population of the cancer cells can escape androgen signaling shutdown and continue to proliferate. In one of the escape pathways, enhanced activity of the key signaling enzyme phosphatidylinositol-3-kinase (P13-K), is observed. So, despite the demonstrated anticancer activities of inositol, enhanced activity of an enzyme that acts on downstream metabolites of inositol., P13-K, may play a role in proliferation of cancer cells. The activity of P13-K is normally important for several vital physiological processes including cytoskeleton arrangement, and insulin signaling. However, it appears that when out of control, and showing over-activity, the enzyme is implicated in disease progression. But then, it is seen that there are enzyme control processes available, including the action of quercitin in (a) inhibiting P13-K activity, and (b) in inhibiting the enzyme pathway generating the most active agonist for the androgen receptor, 5 alpha-dihydrotestosterone, and also for phytic acid in inhibiting P13-K activity. Chemotherapeutic, or prophylactic, approaches to prostate cancer treatment can then involve a combination of natural products—inositol, phytic acid, quercitin—delivered in appropriate temporal manner.

Since cells of any tissue type are rarely, if ever, synchronized so that all cells of the tissue are all in the same phase of the cell cycle at the same time, a means of retaining the beneficial effects of quercitin (along with other flavonoids) and inositol phosphates takes separately, but then adding an enhanced synergistic effect, would be to deliver these compounds in a time controlled manner, first one group, and then, after a time interval, the other group.

There are several approaches to carrying out this strategy. In one approach, the inositol, inositol phosphates and flavonoids which have been extracted and concentrated from an almond fruit mesoderm extract (either aqueous extract of supercritical $CO_2$ extract), are absorbed into the mesoderm fiber extract. This fiber extract is a mixture of soluble and insoluble celluloses and hemicelluloses, and high molecular weight polyphenolics. The inositols, inositol phosphates and flavonoid molecules will be bound to this substrate at different strengths of affinity due to salt bridges, van der Waals forces, and other dipole-dipole interactions. The differing levels of strength of binding will lead to differing rates of release of the active compounds as the fiber traverses the gastrointestinal tract.

A second approach is to encapsulate either the flavonoids or the inositol phosphates group of molecules in a matrix of chemically modified cellulosics, such as the hydrophyllic excipients carboxymethyl cellulose (CMC), hydroxyethylcellulose (HEC), hydroxypropylmethylcellulose (HPMC), along with the hydrophobic excipients such as glyceryl monostearate, or carnauba wax, and with perhaps an overlayering enteric coating of a polymethacrylate. Thus one group of active molecules will be available for absorption and systemic circulation prior to the release for circulation of the other group. Other well known controlled release excipients and coating molecules may be used, and some combinations may be shown to be more effective than others, depending upon the cell types that are the target molecules, e.g. tumor cells of reproductive organs may well be expected to respond differently than cells of digestive organs, or cells of muscle and skeleton.

The mixture of controlled release molecules and free molecules can be presented together as a powder, or as tablets. The concentration of each group of molecules on a weight/weight basis can vary from 100% pure active molecule, as could be the case for pure inositol, which has an enormously high $LD_{50}$, such that an adult could safely ingest approximately 500 grams per day or more, to perhaps as low as 1%–10% active molecules in controlled release matrix, such that perhaps only 1 mg. to 50 grams per day would be safe and efficacious.

An even simpler approach is to prepare a concentrate of the almond fruit aqueous extract to between 55 degrees to 85 degrees Brix, containing inositol, phytic acid, quercitin, and other almond fruit low molecular weight polyphenolics (M.W. less than 600), lignin like higher molecular weight polyphenolics (M.W. greater than 800), as well as sorbitol, organic acids, amino acids, and minerals. The fermentable sugars will have been removed in a 10–24 your batch fermentation with a food grade yeast, such as *S. cerevisiae, S. Pombe, Schwannomyces Castelii,* and *S. Boulardii*. This batch fermentation will have been carried out with an almond fruit extract of between 15 degrees to 35 degrees Brix concentration, followed by removal of spent yeast via centrifugation or macro filtration in the $0.5_u$–$2.0_u$ cutoff range. Removal of the sugars allows for a syrup with higher concentration of the desired components, more readily converted to a dry powder via spray drying or vacuum drum drying. An example of such a dry powder can contain approximately 40% phytic acid, 15% inositol, 20% sorbitol, 0.08% quercitin and other low molecular weight polyphenolics, 5% high molecular weight polyphenolics, 2% organic acids, 5%–10% water. Such a dry powder extract concentrates several of the synergistically acting components of the almond fruit in one composition which can have disease prevention action.

The synergistically acting components of the concentrate will also be acting in a naturally sequential manner, as free inositol will be near completely absorbed into the blood from the small intestine, to be followed later by additional inositol absorbed from large intestine and colon after bacterial conversion of phytic acid to inositol and inositol phosphates. Free polyphenols, such a quercitin, will likewise be absorbed from the small intestine, along with a smaller amount of the glycated quercitin, most of the latter to be enzymatically reduced to the free polyphenol, at a later time, in the large intestine, and made available to the systemic blood system. It is current thinking that the superior beneficial effects of ingesting whole fruits, as contrasted to ingested single pure components is in fact due to the synergy of the temporally acting phytochemical ingredients.

This invention is not to be limited by the by the embodiments shown in the drawings and described in the description, which are given by way of example and not of limitation, but only in accordance with the scope of the appended claims:

I claim:

1. A nutraceutical preparation for ingestion in the human body derived entirely and solely from almond hulls, said almond hulls comprising fiber, water soluble sugars, and water soluble, nutraceuticals as ingredients, said water soluble nutraceuticals being present in said preparation in the same concentration relative to each other as they were in the almond hulls from which they were extracted, and with the same chemical identity as they had while in the almond hulls, some of said water soluble nutraceuticals having pharmacological effects in the human body, alone or in combination with other of said water soluble nutraceuticals, said nutraceutical preparation being derived from almond hulls by the following process:
   a. subjecting said almond hulls to aqueous extraction to produce a water extract containing said water soluble sugars and water soluble nutraceuticals, accompanied by said fibers;
   b. separating said fibers from said water extract;
   c. adding to said water extract a sufficient quantity of a yeast of a type which consumes said water soluble sugars without substantial effect on the chemical identity, or on the amount of, or on the relative concentration of said water soluble nutraceuticals, and permitting said water extract and yeast to ferment so that substantially all of said soluble sugars are consumed by the yeast and yeast solids are produced by the yeast;
   d. removing said yeast solids, whereby to produce an aqueous treated extract containing said nutraceutical preparation; and
   e. removing a substantial portion of the water from said treated extract to provide said nutraceutical preparation in the form of an extract tolerable to a human being.

2. A nutraceutical preparation for ingestion in the human body derived entirely and solely from almond hulls, said almond hulls comprising fiber, water soluble sugars, and water soluble nutraceuticals as ingredients, said water soluble nutraceuticals being present in said preparation in this same concentration relative to each other as they were in the almond hulls from which they were extracted, and with the same chemical identity as they had while in the almond hulls, some of said water soluble nutraceuticals having pharmacological effects in the human body, alone or in combination with other of said water soluble nutraceuticals, said nutraceutical preparation being derived from almond hulls by the following process:
   a. subjecting said almond hulls to aqueous extraction of water soluble nutraceuticals, accompanied by said fibers;
   b. separating said fibers from said water extract;
   c. adding to said water extract a sufficient quantity of a yeast of a type which consumes said water soluble sugars without substantial effect on the chemical identity, or on the amount of, or on the relative concentration of said water soluble nutraceuticals, and permitting said water extract and yeast to ferment so that substantially all of said soluble sugars are consumed by the yeast and yeast solids are produced by the yeast;
   d. removing said yeast solids, whereby to produce an aqueous treated extract containing said nutraceutical preparation; and
   e. drying said treated extract to provide said nutraceutical preparation as a powder or pill.

* * * * *